US009054490B2

(12) United States Patent
Iwase

(10) Patent No.: US 9,054,490 B2
(45) Date of Patent: Jun. 9, 2015

(54) TUNABLE LASER AND PHOTOACOUSTIC DEVICE INCLUDING THE SAME

(71) Applicant: Canon Kabushiki Kaisha, Tokyo (JP)

(72) Inventor: Hideo Iwase, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/149,364

(22) Filed: Jan. 7, 2014

(65) Prior Publication Data

US 2014/0192828 A1    Jul. 10, 2014

(30) Foreign Application Priority Data

Jan. 8, 2013 (JP) ................................ 2013-001118

(51) Int. Cl.
*H01S 3/10* (2006.01)
*H01S 3/106* (2006.01)
*A61B 5/00* (2006.01)
*H01S 3/08* (2006.01)
*H01S 3/137* (2006.01)
*H01S 3/16* (2006.01)

(52) U.S. Cl.
CPC ........... *H01S 3/1062* (2013.01); *H01S 3/08027* (2013.01); *H01S 3/137* (2013.01); *H01S 3/08036* (2013.01); *H01S 3/1623* (2013.01); *H01S 3/1635* (2013.01); *A61B 5/0095* (2013.01)

(58) Field of Classification Search
CPC .. H01S 3/08027; H01S 3/08036; H01S 3/137
USPC ........................................................ 372/20
See application file for complete search history.

(56) References Cited

U.S. PATENT DOCUMENTS

| 3,868,592 | A | * | 2/1975 | Yarborough et al. | ......... 372/105 |
| 5,107,509 | A | * | 4/1992 | Esterowitz et al. | ............. 372/20 |
| 2007/0015992 | A1 | * | 1/2007 | Filkins et al. | ................. 600/407 |

FOREIGN PATENT DOCUMENTS

JP    2002-232047 A    8/2002

OTHER PUBLICATIONS

Harris, "Optical Network Synthesis Using Birefringent Crystals. I. Synthesis of Lossless Networks of Equal-Length Crystals," Oct. 1964, Journal of the Optical Society of America, vol. 54, No. 10, pp. 1267-1279.*
"The birefringent filter" by John W. Evans, in Journal of the Optical Society of America, vol. 39, issue 3, pp. 229-237 (1949).

* cited by examiner

*Primary Examiner* — Yuanda Zhang
*Assistant Examiner* — Michael Carter
(74) *Attorney, Agent, or Firm* — Canon USA Inc. IP Division

(57) ABSTRACT

A tunable laser includes a resonator including a highly reflecting mirror and a partially reflecting mirror; a gain medium disposed in the resonator; a birefringence filter disposed in the resonator; and an excitation device that excites the gain medium. In the tunable laser, light that passes through the birefringence filter oscillates between the highly reflecting mirror and the partially reflecting mirror. An oscillation wavelength is switched by rotating the birefringence filter. The birefringence filter includes a first birefringent plate and a second birefringent plate, which have principal dielectric axes parallel to optical surfaces thereof. An absolute value of an angle formed by the principal dielectric axis of the first birefringent plate and the principal dielectric axis of the second birefringent plate is larger than zero.

20 Claims, 14 Drawing Sheets

OSCILLATION AT 1ST SUBPEAK

WAVELENGTH VARIABLE RANGE
$\lambda \leq 786$ nm

WAVELENGTH VARIABLE RANGE
λ ≤ 796 nm

TUNABLE LASER AND PHOTOACOUSTIC DEVICE INCLUDING THE SAME

BACKGROUND OF THE INVENTION

1. Field of the Invention

The present invention relates to a tunable laser including a birefringence filter and a photoacoustic device including the tunable laser.

2. Description of the Related Art

Tunable laser light sources have been widely used in various fields including medical and measurement fields and actively been studied. With the photoacoustic tomography (PAT), distribution of light absorption, that is, distribution of objects in a living body can be imaged by, for example, irradiating the living body with light of a wavelength band in the range of 700 to 900 nm, which is less likely to be absorbed by water, and detecting an acoustic wave that occurs as a result of the light being absorbed by the objects in the living body. A tunable laser light source having the following configuration is known. The light source includes a gain medium having a stimulated-emission cross-section in a desired waveband and switches the oscillation wavelength using a birefringence filter.

FIG. 11 schematically illustrates a configuration of a tunable laser light source including an existing birefringence filter. A partially reflecting mirror 105 and a highly reflecting mirror 104 form a resonator. Part of light emitted from a gain medium 109 excited by an excitation device 110 is caused to oscillate by the resonator and the gain medium 109. Part of the oscillating light (beam) passes through the partially reflecting mirror 105 and is taken to the outside as an output.

The birefringence filter includes one or more birefringent plates superposed parallel to one another such that their crystal principal dielectric axes (principal axes of refraction ellipsoids) coincide with one another. The birefringence filter is arranged such that an angle (insertion angle) θ formed by an optical axis 107 of a beam and the normal to the birefringence filter coincides with Brewster angle $\theta_B$ of the birefringent plates.

At this time, the reflectivity of p-polarized light 106 that is to be reflected off the surfaces of the birefringent plates is zero, and thus the transmission of the p-polarized light 106 (which is parallel to the surface of FIG. 11) that passes through the birefringence filter at the transmission peak of the birefringence filter is approximately one (100%). On the other hand, s-polarized light 108 is reflected off the surfaces of the birefringent plates and thus is lost through the reflection to a larger extent than the p-polarized light 106, whereby the s-polarized light 108 does not substantially contribute to oscillation.

The following description is given considering only a component of light incident on the birefringence filter as p-polarized light (having an electric field intensity Epin) and a component (having an electric field intensity Epout) that transmits as p-polarized light among transmission light components.

The transmission and transmission spectrum of the birefringence filter are defined by the electric field intensity ratio $(Epout)^2/(Epin)^2$. In the transmission spectrum of the birefringence filter, the peak of the transmission at which the transmission is approximately one is called a transmission peak.

The oscillation wavelength is switched by changing the wavelength at the transmission peak of the birefringence filter. Specifically, the wavelength at the transmission peak is shifted by rotating the birefringence filter around the normal (having a rotation angle φ in FIG. 11) to the optical surface of the birefringence filter. In the configuration illustrated in FIG. 11, the transmission at the shifted transmission peak can be maintained at one. The details of the configuration of the birefringence filter and a method of switching the oscillation wavelength are described in "the birefringent filter" by John W. EVANS, in Journal of the Optical Society of America, vol. 39, issue 3, pp. 229-237 (1949) and Japanese Patent Laid-Open No. 2002-232047.

FIG. 12 and FIG. 13 are graphs for describing the number of birefringent plates appropriate for a tunable laser light source.

FIG. 12 illustrates a transmission spectrum of a birefringence filter including one birefringent plate. The transmission spectrum has multiple peaks at which the transmission is one. An interval Δλ between the transmission peaks is substantially in inverse proportion to the thickness d of the birefringent plate and the full width δλ at half maximum corresponding to the transmission peak is approximately Δλ/2. Generally, the thickness d of the birefringent plate is selected such that the interval Δλ is larger than the width of a wavelength variable range and thus the full width δλ at half maximum corresponding to the transmission peak is larger than the half of the width of the wavelength variable range.

Meanwhile, the tunable laser light source is required to have a sufficiently smaller full width δλ at half maximum corresponding to the transmission peak than the wavelength variable range in order to stabilize the oscillation wavelength. Thus, the configuration including one birefringent plate illustrated in FIG. 13 cannot maintain a stable oscillation wavelength.

FIG. 13 illustrates transmission spectra of the birefringence filters respectively including two, three, and four birefringent plates. The thicknesses of the second, third, and fourth birefringent plates are respectively two, three, and four times the thickness d of the thinnest birefringent plate. In this configuration, an interval Δλ between transmission peaks is substantially in inverse proportional to the thickness d of the thinnest birefringent plate.

In the case where the birefringence filter includes two birefringent plates, the full width δλ at half maximum corresponding to the transmission peak is approximately ⅙ the interval Δλ between the transmission peaks. Thus, the thickness d of the birefringent plate can be selected such that the interval Δλ between the transmission peaks is wider than the width of the wavelength variable range and the full width δλ at half maximum corresponding to the transmission peak is sufficiently smaller than the width of the wavelength variable range, thereby enabling stable oscillation switching. As illustrated in FIG. 13, an increase in number of birefringent plates enables further reduction in full width δλ at half maximum corresponding to the transmission peaks.

As the number of birefringent plates increases, however, an adjustment of crystal principal axes of birefringent plates becomes more difficult, thereby increasing the production cost of birefringent plates. For this reason, in a tunable laser light source, in which having a characteristic of stable wavelength switching regardless of a spectrum width of oscillating beams is regarded as important, a birefringence filter including two birefringent plates is preferred.

SUMMARY OF THE INVENTION

A tunable laser includes a resonator including a highly reflecting mirror and a partially reflecting mirror; a gain medium disposed in the resonator; a birefringence filter disposed in the resonator; and an excitation device that excites the gain medium. In the tunable laser, light that passes through the birefringence filter oscillates between the highly reflecting mirror and the partially reflecting mirror. An oscillation wavelength is switched by rotating the birefringence filter. The birefringence filter includes a first birefringent plate and a second birefringent plate, which have principal dielectric axes parallel to optical surfaces thereof. An absolute value of an angle formed by the principal dielectric axis of the first birefringent plate and the principal dielectric axis of the second birefringent plate is larger than zero.

Further features of the present invention will become apparent from the following description of exemplary embodiments with reference to the attached drawings.

DESCRIPTION OF THE EMBODIMENTS

Figure 13:
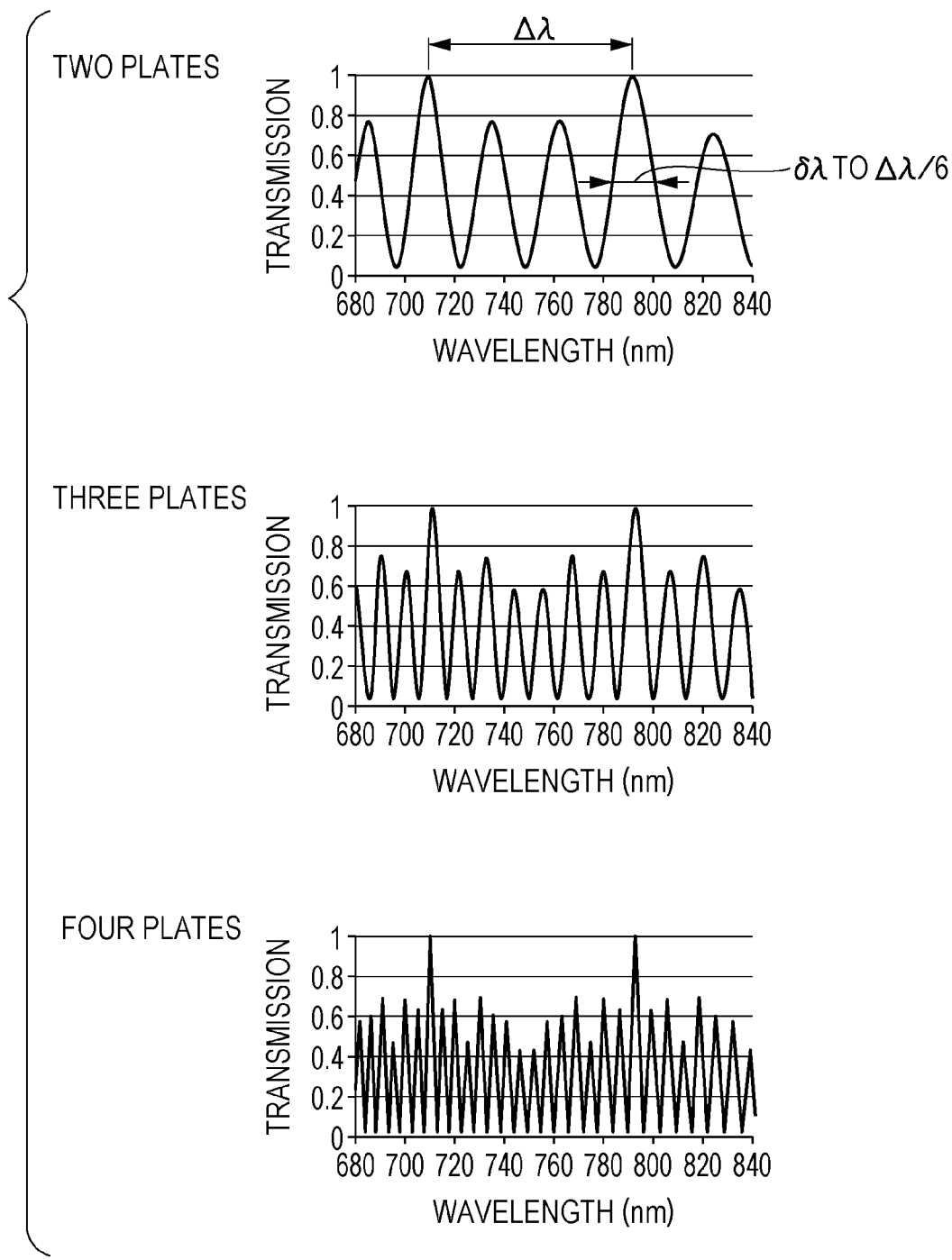
FIG. 13 illustrates transmission spectra of birefringence filters in the cases where the number of birefringent plates is increased.

Now, the configuration including a birefringence filter including two birefringent plates superposed such that their principal dielectric axes are not shifted from each other is studied in consideration of production cost and for stable wavelength switching. As illustrated in FIG. 13, the transmission increases at the second high peaks (hereinafter referred to as subpeaks), at which the transmission is second high and which appear between the transmission peaks. Such subpeaks at which the transmission is high cause unnecessary oscillation and limit the wavelength variable range. Hereinbelow, this problem will be described referring to FIGS. 15A and 15B.

Figure 14A:
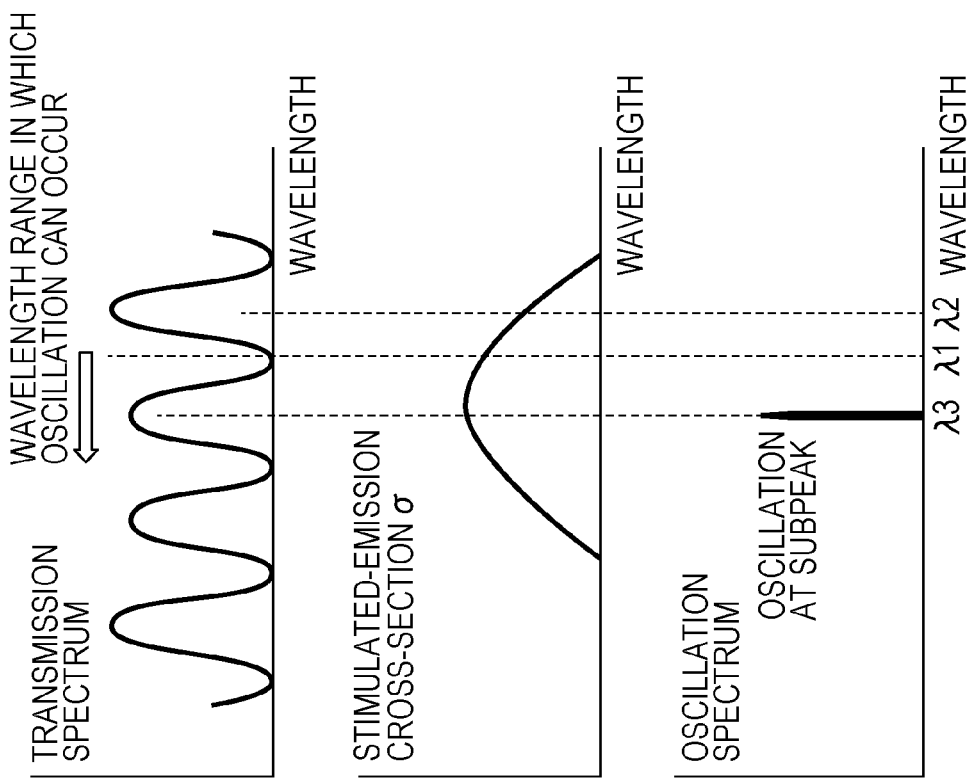
FIGS. 14A and 14B illustrate a problem to be solved in the invention.
Figure 14B:
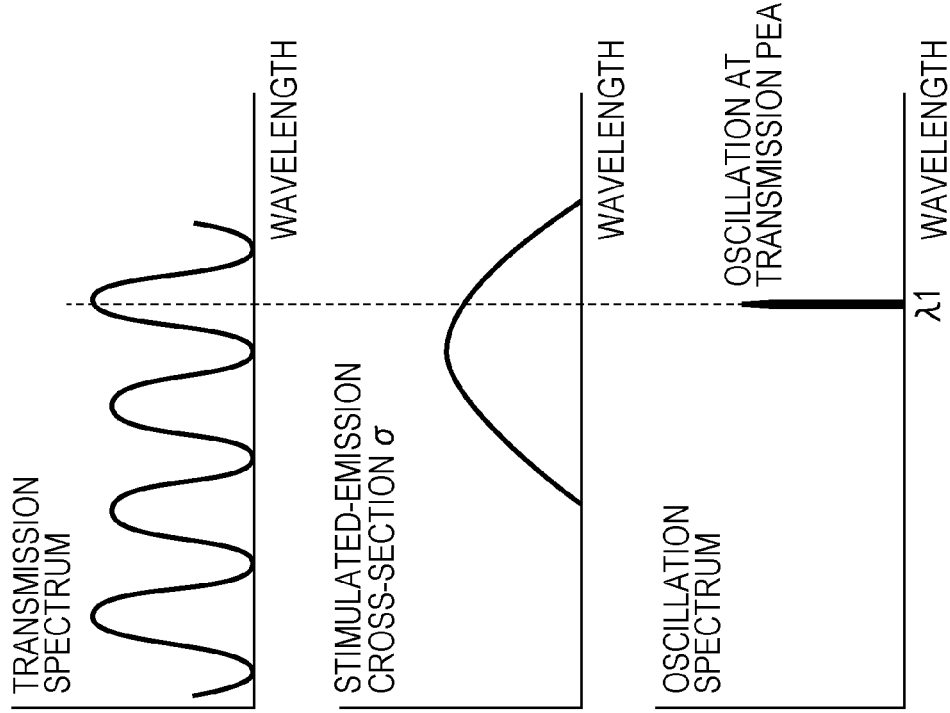

FIGS. 14A and 14B each illustrate a transmission spectrum of a birefringence filter including two birefringent plates, wavelength dependency of a stimulated-emission cross-section of a gain medium, and a spectrum of lasing beams (lasing spectrum). The birefringence filters relating to FIGS. 14A and 14B have different rotation angles $\phi$ and thus the transmission peaks are shifted from each other. Each of the transmission spectra of these birefringence filters has transmission peaks, at which the transmission is one, and subpeaks, which appear between the transmission peaks.

A threshold excited electron density Nth at which the gain of a gain medium and a loss of a resonator are evenly balanced and that is required for lasing in a certain wavelength is calculated by the following expression (1):

$$2 \times \sigma \times Nth \times L = \ln(1/R) + 2 \times \ln(1/T) \qquad (1).$$

Here, the stimulated-emission cross-section at the wavelength is denoted by $\sigma$, the length of the gain medium is denoted by L, the transmission of a partial transmission mirror is denoted by R, and the transmission of a birefringence filter is denoted by T.

In FIG. 14A, the transmission peak is located at a wavelength $\lambda 1$ at which the stimulated-emission cross-section $\sigma$ is relatively high. In this case, the threshold excited electron density Nth is smallest at the wavelength $\lambda 1$ and oscillation occurs if the excited electron increases. Generally, when oscillation occurs at a certain transmission peak, the excited electron density N is kept at a uniform value and oscillation does not occur at other transmission peaks. Thus, light having a wavelength $\lambda 1$ can be selectively caused to oscillate in FIG. 14A.

In FIG. 14B, on the other hand, the wavelength at the transmission peak is shifted from $\lambda 1$ to $\lambda 2$ ($\lambda 1 < \lambda 2$) by rotating the birefringence filter. Here, the wavelength at the subpeak is shifted to a wavelength $\lambda 3$ ($\lambda 3 < \lambda 1$). Hereinbelow, the transmission at the transmission peaks is denoted by Tmain, the transmission at the subpeaks is denoted by Tsub, the stimulated-emission cross-section at the wavelength $\lambda 2$ is denoted by $\sigma(\lambda 2)$, and the stimulated-emission cross-section at the wavelength $\lambda 3$ is denoted by $\sigma(\lambda 3)$. The threshold excited electron densities at the wavelengths $\lambda 2$ and $\lambda 3$ obtained by the expression (1) are respectively denoted by Nth ($\lambda 2$) and Nth ($\lambda 3$).

From the expression (1), it is found that Nth ($\lambda 3$) < Nth ($\lambda 2$) as long as $\sigma(\lambda 3)$ is sufficiently larger than $\sigma(\lambda 2)$. This means that oscillation occurs at the subpeak wavelength $\lambda 3$, not at the wavelength at the transmission peak.

This oscillation at the subpeak disturbs oscillation at the transmission peak, which is at the wavelength λ2, and limits the wavelength variable range.

As described above, a birefringence filter including two birefringent plates has problems in that oscillation is highly likely to occur at the wavelengths at the subpeaks and the wavelength variable range is limited because the birefringence filter has a transmission spectrum in which the transmission is relatively high at the subpeaks.

The present invention provides a tunable laser in which a birefringence filter including two birefringent plates enables reduction of the transmission at a subpeak and in which a wavelength variable range can be expanded.

A tunable laser according to an embodiment of the present invention, a tunable laser in which a wavelength variable range can be expanded can be formed by shifting, in a birefringence filter including two birefringent plates, the principal dielectric axes of a first birefringent plate and a second birefringent plate such that the transmission Tsub at the subpeak at which (σsub−σmain)/σmain is largest among all subpeaks is reduced, where the stimulated-emission cross-sections at the transmission peak and the subpeak of the birefringence filter are denoted by σmain and σsub, respectively.

Now, a tunable laser according to an embodiment will be described referring to the drawings.

First Embodiment

Figure 1A:
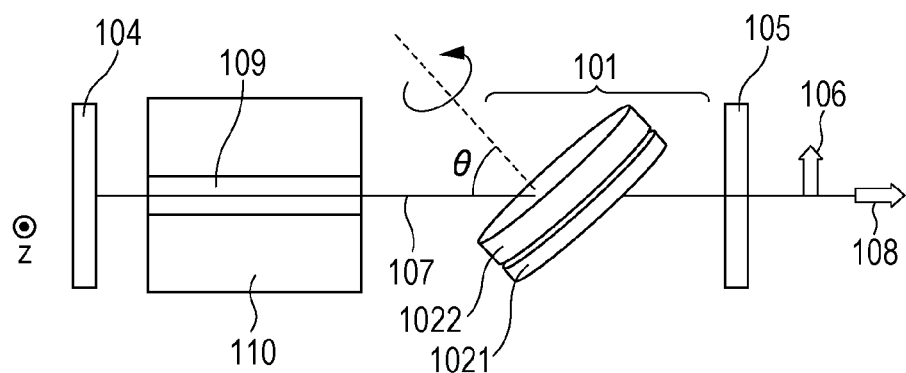
FIGS. 1A and 1B schematically illustrate a configuration example of a tunable laser according to first and second embodiments of the present invention.
Figure 1B:
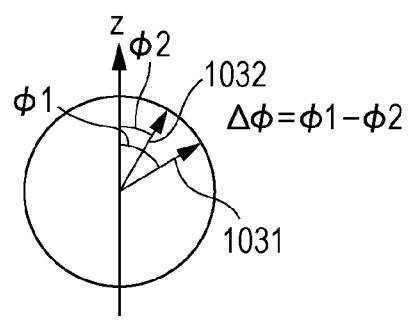

Referring to FIGS. 1A and 1B, a configuration example of a tunable laser according to a first embodiment is described.

FIG. 1A illustrates a schematic of a tunable laser according to an embodiment. The tunable laser according to the embodiment includes a resonator, a gain medium 109 inside the resonator, an excitation device 110 that excites the gain medium, and a birefringence filter 101. The resonator includes a highly reflecting mirror 104 and a partially reflecting mirror 105 having a reflectivity R. In the laser, beams that propagate between the highly reflecting mirror 104 and the partially reflecting mirror 105 and pass through the birefringence filter oscillate.

Here, the highly reflecting mirror is a mirror having a reflectivity with which the mirror reflects 98% or more, preferably 99.5% or more of light having a wavelength range emitted from a light source. In addition, the partially reflecting mirror is a mirror having a reflectivity with which the mirror reflects 50% to 90%, preferably 50% to 70% of light having a wavelength range emitted from a light source.

The birefringence filter 101 includes a first birefringent plate 1021 and a second birefringent plate 1022. FIG. 1B illustrates the birefringence filter 101 when viewed in a direction of the normal to the optical surface of the birefringence filter 101 (in a direction indicated by the dotted line in FIG. 1A). The principal dielectric axes 1031 and 1032 of the birefringent plates 1021 and 1022 are parallel to the optical surfaces of the birefringent plates. In FIG. 1B, an angle formed by the z-axis direction and the principal dielectric axis 1031 of the first birefringent plate 1021 is denoted by φ1 and an angle formed by the z-axis direction and the principal dielectric axis 1032 of the second birefringent plate 1022 is denoted by φ2.

The first birefringent plate and the second birefringent plate are superposed such that their principal dielectric axes are shifted at a shift angle Δφ. Here, the shift angle Δφ is defined by a difference between a rotation angle φ1 of the first birefringent plate and a rotation angle φ2 of the second birefringent plate (Δφ=φ2−φ1) and can take a negative value.

The birefringence filter is installed at a position on the optical axis such that an angle (insertion angle θ) formed by the normal to the optical surface of the birefringence filter and an optical axis of the beam is Brewster's angle θB. For example, when the birefringent plates are made of crystal and alexandrite crystal is used as a gain medium, the oscillation wavelength is 700 to 850 nm and Brewster's angle of the crystal at this time is approximately 57°.

The birefringence filter is mounted on a rotating mechanism that rotates the first birefringent plate and the second birefringent plate together or individually. The rotation angle φ of the birefringence filter is defined by an angle formed by an axis that is rotated at 45° in such a direction as to shift the principal dielectric axis 1031 of the first birefringent plate 1021 from the z axis and a bisector that bisects an angle between the principal dielectric axis 1031 of the first birefringent plate 1021 and the principal dielectric axis 1032 of the second birefringent plate 1022.

Figure 3A:
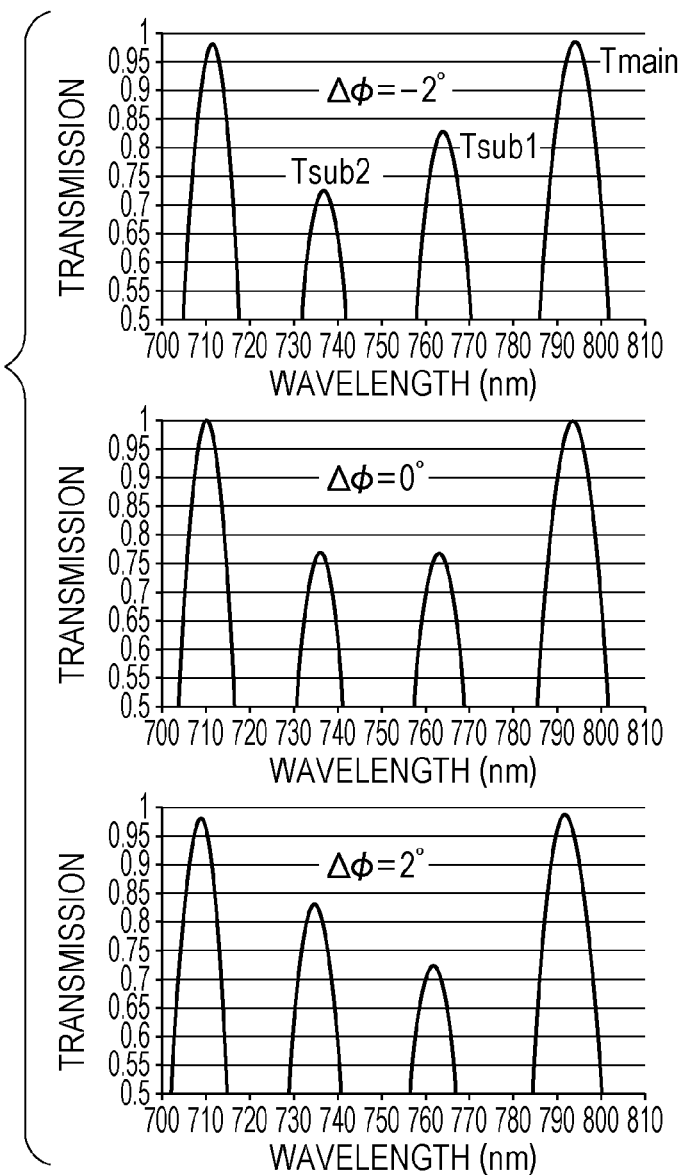
FIG. 3A illustrates the transmission spectrum when the shift angle of the birefringence filter according to the first embodiment of the present invention is changed and FIG. 3B illustrates the transmission ratio.

FIG. 3A illustrates transmission spectra in the cases where the birefringence filter has two birefringent plates respectively having thicknesses of d and 2d, where d=0.762 mm and the shift angle Δφ is changed among −2°, 0°, and +2°. Two subpeaks that appear between transmission peaks (main peaks) are referred to as a first subpeak and a second subpeak in order from the one having the largest frequency.

Figure 3B:
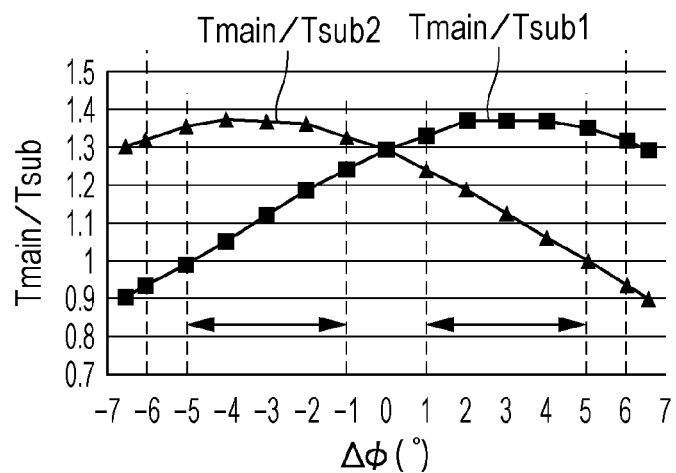

FIG. 3B illustrates a relationship between the shift angle Δφ and a ratio of the transmission Tmain of the transmission peak to the transmission Tsub1 of the first subpeak or a ratio of the transmission Tmain of the transmission peak to the transmission Tsub2 of the second subpeak.

As is found from FIG. 3B, the transmission at the first subpeak or the second subpeak decreases as a result of changing the shift angle Δφ to a positive or negative value. In other words, changing the shift angle Δφ to a positive or negative value can increase the transmission ratio Tmain/Tsub1 or Tmain/Tsub2.

The first subpeak, the second subpeak, and the transmission peak have different transmissions and stimulated-emission cross-sections. Among the wavelengths at these peaks, the one having the smallest threshold excited electron density Nth oscillates selectively.

On the basis of the expression (1), the condition under which the transmission peak has a smaller threshold excited electron density Nth than a certain subpeak is expressed by the following expression (2):

$$\ln(1/R) \times (\sigma sub - \sigma main)/2\sigma main < \ln(Tmain/Tsub) \qquad (2).$$

Here, R denotes the reflectivity of the partially reflecting mirror and σsub and σmain respectively denote stimulated-emission cross-sections at the subpeak and the transmission peak (main peak).

The expression (2) expresses that oscillation can be made to occur even at the wavelength at the transmission peak, at which oscillation has not been able to occur in the existing configuration, by increasing the ratio Tmain/Tsub by making the stimulated-emission cross-section σsub larger than the stimulated-emission cross-section σmain. In other words, by shifting the principal dielectric axes such that the transmission Tsub of the subpeak at which (σsub−σmain)/σmain is largest among all subpeaks is reduced, the wavelength variable range can be expanded and thus oscillation can occur at the frequency at which oscillation has not been able to occur so far.

As is understood from FIG. 3B, when the shift angle Δφ is 0°<Δφ≤6° or −6°≤Δσ<0°, Tmain/Tsub1 or Tmain/Tsub2 is larger than that in the case where the shift angle Δφ is 0°, whereby an effect of the present invention can be achieved.

Simulations prove that the ratio of the transmission spectrum illustrated in FIG. 3B does not depend on the thickness d of the birefringent plate.

Figure 2A:
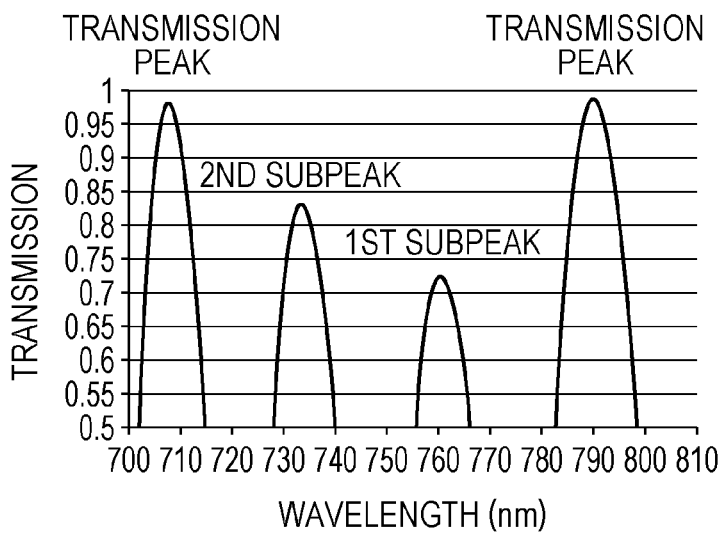
FIGS. 2A and 2B respectively illustrate the transmission spectrum of the birefringence filter according to the first embodiment of the present invention and the stimulated-emission cross-section of the gain medium.
Figure 2B:
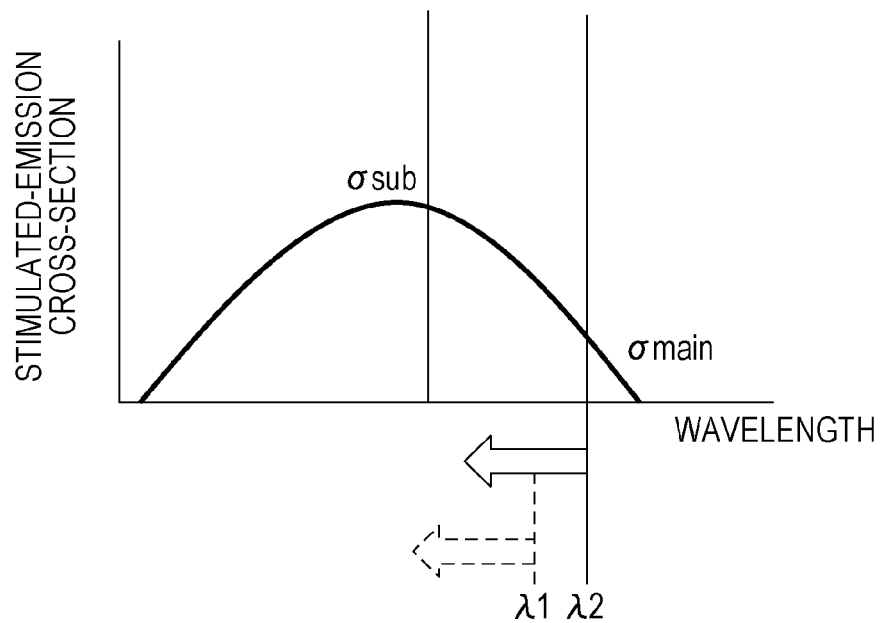

FIG. 2A illustrates a transmission spectrum of a birefringence filter according to the embodiment and FIG. 2B illustrates a stimulated-emission cross-section σ of a gain medium.

The transmission spectrum of the birefringence filter illustrated in FIG. 2A is calculated when the thicknesses of the first birefringent plate and the second birefringent plate are respectively taken as 0.762 mm and 1.524 mm and the shift angle $\Delta\phi$ between the principal dielectric axes is taken as 2°. In the transmission spectrum, transmission peaks (main peaks), at which the transmission is approximately one, appear and two subpeaks, which are a first subpeak and a second subpeak in order from the one having the largest wavelength, appear between the transmission peaks.

As described above, the wavelengths at the transmission peaks and the subpeaks can be shifted relative to one another by rotating the birefringence filter. In addition, the transmission Tsub1 of the first subpeak and the transmission Tsub2 of the second subpeak can be reduced by shifting the principal dielectric axis of the first birefringent plate and the principal dielectric axis of the second birefringent plate from each other. In FIG. 2A, by setting the shift angle $\Delta\phi$ at 2°, the transmission at the first subpeak is reduced.

In the case of a tunable laser including, in combination, the gain medium of FIG. 2B and an existing birefringence filter in which the principal dielectric axes of the first birefringent plate and the second birefringent plate coincide with each other, oscillation occurs at the wavelength at the first subpeak when the transmission peak exceeds the wavelength $\lambda 1$. Thus, the wavelength variable range is limited to a range not exceeding $\lambda 1$ indicated by the dotted arrow. In the embodiment of the present invention illustrated in FIGS. 1A, however, the principal dielectric axis of the first birefringent plate and the principal dielectric axis of the second birefringent plate are shifted from each other in order to reduce the transmission at the first subpeak at which (σsub−σmain)/σmain is largest. Such a tunable laser allows oscillation to occur at the wavelength $\lambda 2$ of the transmission peak, whereby the wavelength variable range can be expanded to the wavelength $\lambda 2$.

In the example illustrated in FIGS. 2A and 2B, (σsub−σmain)/σmain is largest at the first subpeak. Thus, by preventing oscillation from occurring at the first subpeak by shifting the principal dielectric axes such that the shift angle $\Delta\phi$ is positive, oscillation can be made to occur at the wavelength $\lambda 2$ at which oscillation is less likely to occur in the existing configuration.

In the case, on the other hand, where (σsub−σmain)/σmain is largest at the second subpeak, unnecessary oscillation can be prevented from occurring at the second subpeak by shifting the principal dielectric axes such that the shift angle $\Delta\phi$ is negative, whereby the wavelength variable range can be expanded.

Specifically, when transmission peak is at the edge of the wavelength variable range, if the principal dielectric axes of birefringent plates are shifted from each other so as to reduce the transmission at the subpeak at which (σsub−σmain)/σmain is largest, the wavelength variable range can be expanded.

Referring now to experiment data, the first embodiment of the present invention will be specifically described.

Firstly, as a comparative example, the following tunable laser is described. In the tunable laser, a first birefringent plate and a second birefringent plate, which constitute a birefringence filter, are made of crystal plates, superposed such that their principal dielectric axes, which are parallel to the optical surfaces, coincide with each other (at the shift angle $\Delta\phi=0°$), and fixed to each other.

Figures 1, 4A:
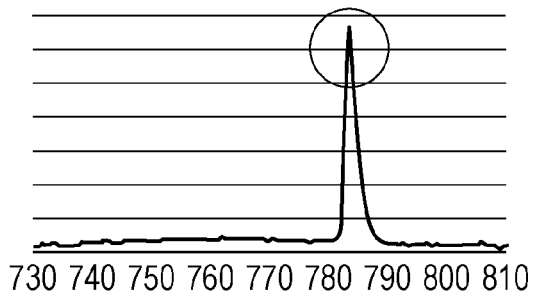
FIG. 4A-1 and 4A-2 illustrate oscillation spectra of comparative examples.
Figures 2, 4A:
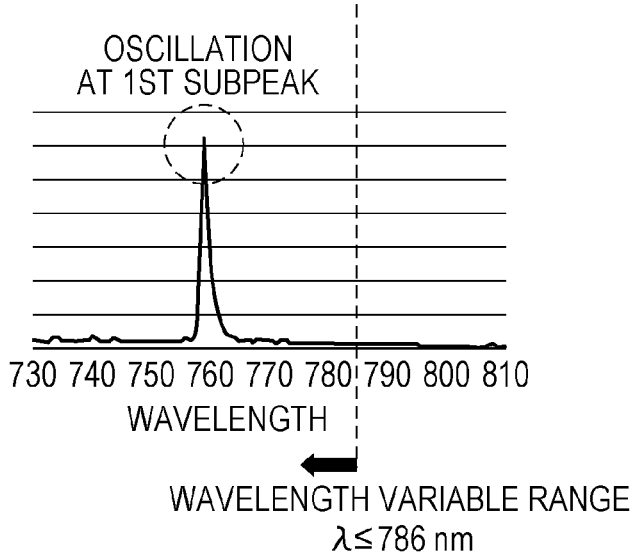

FIGS. 4A-1 and 4A-2 illustrate oscillation spectra of an existing wavelength-variable alexandrite laser in which alexandrite crystal is used as a gain medium. The oscillation spectra of FIGS. 4A-1 and 4A-2 are different from each other with regard to the rotation angle φ of the birefringence filter. This wavelength-variable alexandrite laser is used for medical measurement purposes and is thus required to be able to vary the wavelength in a range of approximately 740 to 800 nm.

In the wavelength variable range, the reflectivity of the highly reflecting mirror is 99% or more and the reflectivity of the partially reflecting mirror is approximately 70%. The highly reflecting mirror and the partially reflecting mirror face each other approximately 45 cm away from each other with the gain medium interposed therebetween.

The thicknesses of the first birefringent plate and the second birefringent plate are 0.762 mm and 1.524 mm, respectively. The birefringence filters are interposed between the gain medium and the partially reflecting mirror such that the normal to the crystal surfaces and the optical axis of the laser form Brewster's angle. Brewster's angle θB of crystal in the wavelength variable range is 57°.

Here, a wavelength interval between the transmission peaks is approximately 90 nm, which is larger than the width of the wavelength variable range (approximately 60 nm).

Figure 4B:
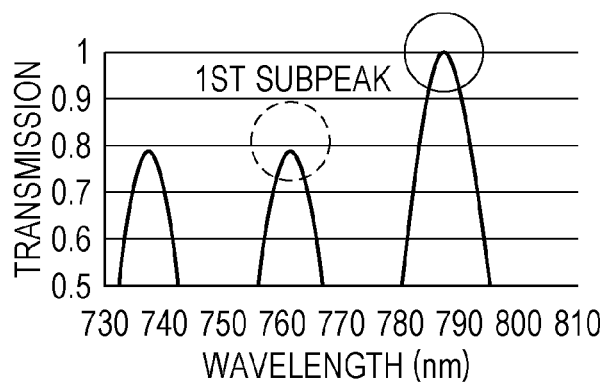
FIG. 4B illustrates a transmission spectrum of the birefringence filter.
Figure 4C:
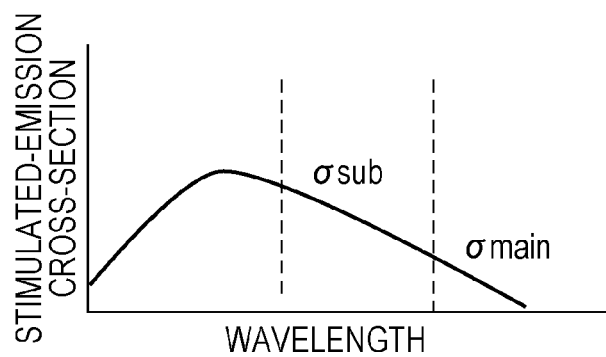
FIG. 4C illustrates the stimulated-emission cross-section of the gain medium.

FIG. 4B illustrates a transmission spectrum of this birefringence filter and FIG. 4C illustrates a stimulated-emission cross-section of alexandrite crystal in the wavelength range illustrated in FIG. 4B.

When the transmission peak is shifted to the longer wavelength side, the difference between the stimulated-emission cross-sections of the first subpeak and the transmission peak, which is σsub−σmain, increases.

As illustrated in FIG. 4A-1, in the existing configuration, oscillation occurred at the wavelength 786 nm as a result of an adjustment of the rotation angle φ of the birefringence filter. However, when the rotation angle φ was adjusted such that the transmission peak is located at a wavelength longer than 786 nm, for example, the wavelength of 787 nm as illustrated in FIG. 4A-2, oscillation occurred at the wavelength of 760 nm, which is at the first subpeak. That is, the wavelength variable range in the existing configuration fell within a range not exceeding 786 nm.

Now, a tunable laser according to the embodiment will be described.

Figure 5A:
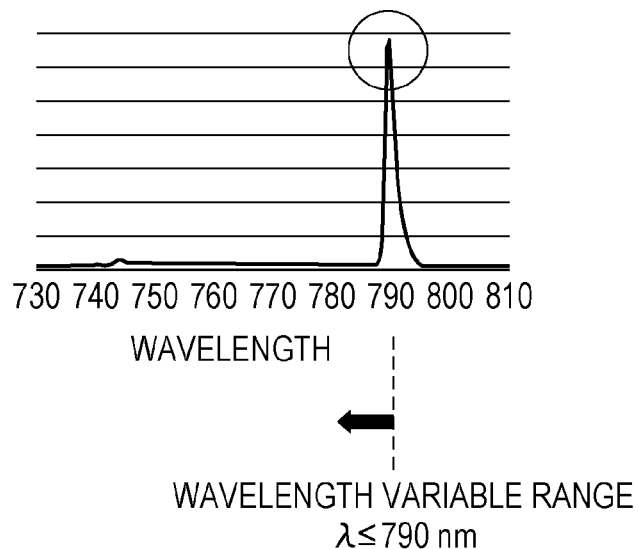
FIG. 5A illustrates an oscillation spectrum of the tunable laser according to the first embodiment of the present invention.
Figure 5B:
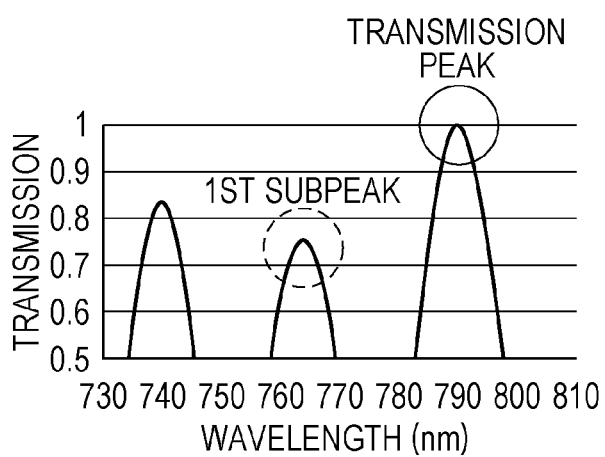
FIG. 5B illustrates a transmission spectrum of the birefringence filter.
Figure 5C:
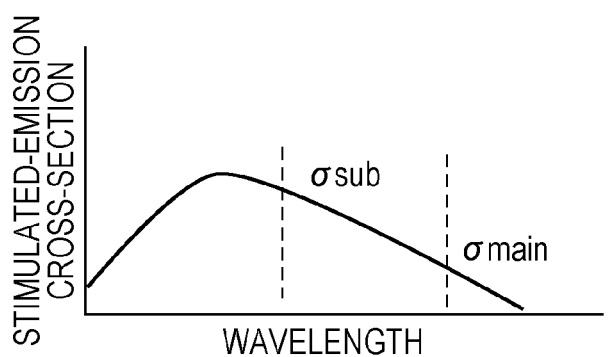
FIG. 5C illustrates the stimulated-emission cross-section of the gain medium.

FIG. 5A illustrates an oscillation spectrum of a tunable laser in which alexandrite crystal is used as a gain medium. At the wavelength of 786 nm or larger, (σsub−σmain)/σmain is largest at a point between the first subpeak and the transmission peak.

Thus, in this embodiment, the principal dielectric axes were shifted such that the transmission at the first subpeak decreases. The shift angle $\Delta\phi$ was set at 2°. Consequently, the transmission at the first subpeak decreased and the ratio of the transmission at the transmission peak to the transmission at the first subpeak, which is Tmain/Tsub1, increased, whereby the longer-wavelength-side edge of the wavelength variable range was capable of being expanded to 790 nm.

Although the results of experiments conducted when the shift angle $\Delta\phi$ is set at 2° have been described above, an effect of the present invention can be achieved even when the shift angle $\Delta\phi$ is smaller than 2°.

For example, in the case of designing a tunable laser in which alexandrite crystal is used as a gain medium and the wavelength variable range approximately ranges from 740 to 800 nm, the difference between stimulated-emission cross-sections $(\sigma sub-\sigma main)/\sigma main$ is larger than or equal to 0.8.

When the reflectivity R of the partially reflecting mirror is lower than or equal to 0.5, the relationship of the expression (2) is satisfied if Tmain/Tsub>1.32. As is found from FIG. 3B, the shift angle $\Delta\phi$ that satisfies Tmain/Tsub>1.32 is $5°\geq|\Delta\phi|\geq1°$ (in the ranges of the shift angle $\Delta\phi$ indicated by solid arrows in FIG. 3).

Although the case where the wavelength variable range ranges approximately from 740 to 800 nm is described in this embodiment, the wavelength variable range may be a different wavelength range.

For example, in the case of designing a tunable laser in which alexandrite crystal is used as a gain medium and the wavelength variable range ranges approximately from 720 to 670 nm, the subpeak located at the edge of the wavelength variable range and at which $(\sigma sub-\sigma main)/\sigma main$ is largest is a second subpeak. Thus, the wavelength variable range can be expanded by shifting the principal dielectric axes of two birefringent plates at the shift angle $\Delta\phi$ of, for example, $-3°$ such that the transmission at the second subpeak is reduced.

Second Embodiment

A configuration example of a tunable laser according to a second embodiment is described referring to FIGS. 1A and 1B. The tunable laser according to the second embodiment is different from the tunable laser according to the first embodiment in terms that the insertion angle of the birefringence filter is not Brewster's angle. Part of the configuration similar to that of the first embodiment will be appropriately omitted.

In FIG. 1, the birefringence filter is installed at a position on the optical axis 107 of the beam such that an angle (insertion angle $\theta$) formed by the normal to the optical surface of the birefringence filter and the optical axis 107 is smaller than Brewster's angle $\theta B$.

For example, when the birefringent plates are made of crystal and alexandrite crystal is used as a gain medium, the oscillation wavelength falls within a range of 700 to 850 nm and Brewster's angle of crystal at this time is approximately 57°. In this case, the insertion angle $\theta$ is smaller than 57°.

Figure 6A:
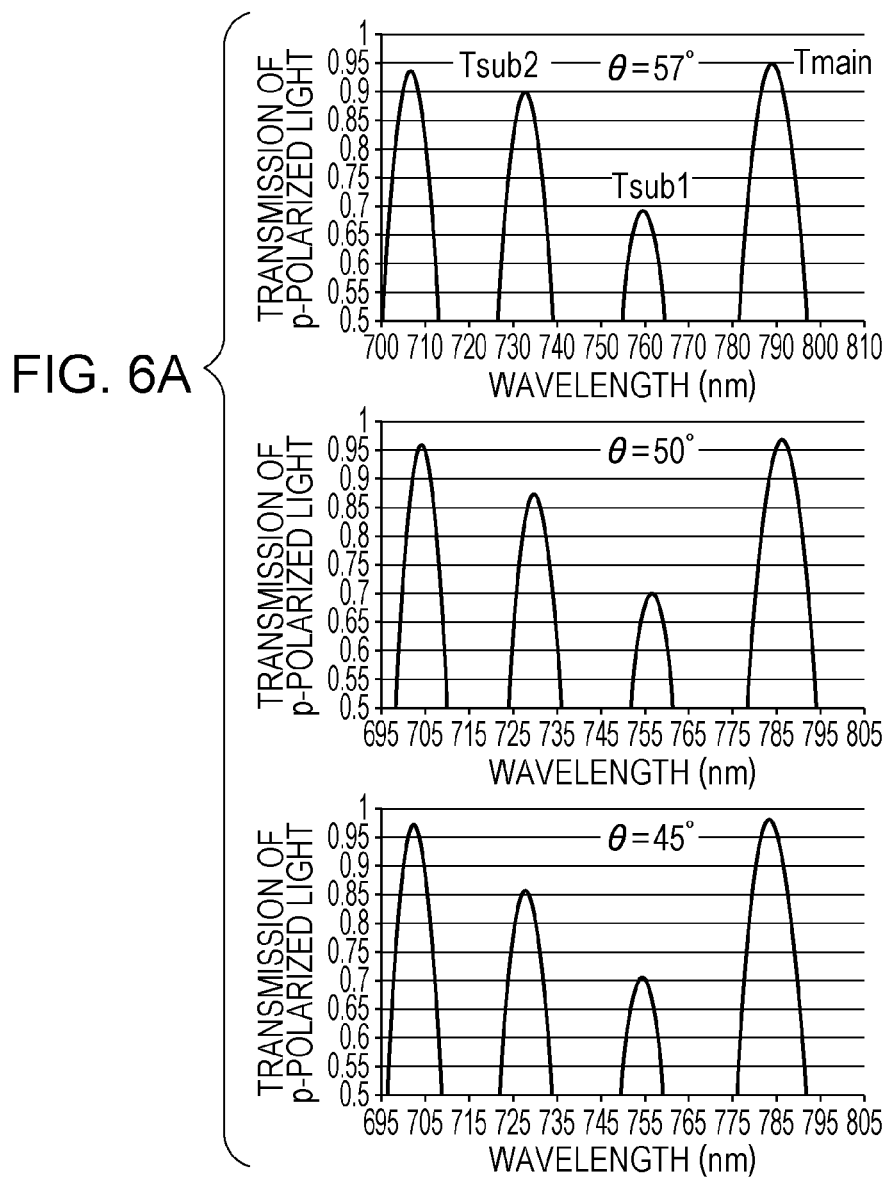
FIG. 6A illustrates transmission spectra in the cases where the insertion angle is changed according to a second embodiment of the present invention.

FIG. 6A illustrates transmission spectra in the cases where the shift angle $\Delta\phi$ between the principal dielectric axis of the first birefringent plate and the principal dielectric axis of the second birefringent plate is set at 4° and the insertion angle $\theta$ is changed between 57° $(=\theta B)$, 50°, and 45°.

Figure 6B:
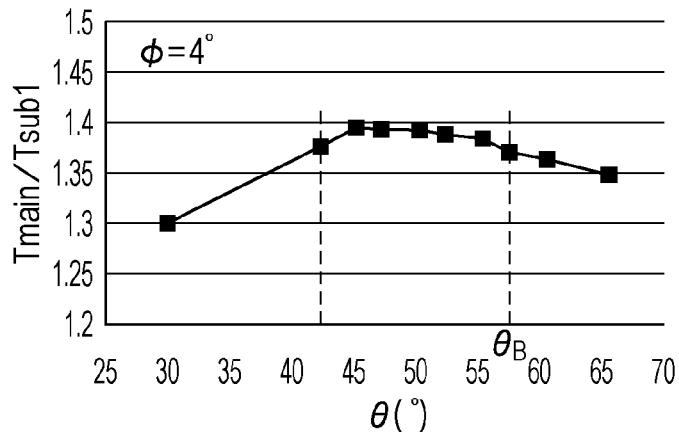
FIG. 6B illustrates the ratio of the transmission of the transmission peak to the transmission of the subpeak according to the second embodiment.

FIG. 6B is a graph illustrating a relationship between the insertion angle $\theta$ and the ratio of the transmission at the transmission peak to the transmission at the first subpeak Tmain/Tsub1 when the shift angle $\Delta\phi$ is 4°. It is found that the transmission ratio Tmain/Tsub1 increases in a range of $42°\leq\theta<\theta B$, where the insertion angle $\theta$ is smaller than Brewster's angle.

Figure 7:
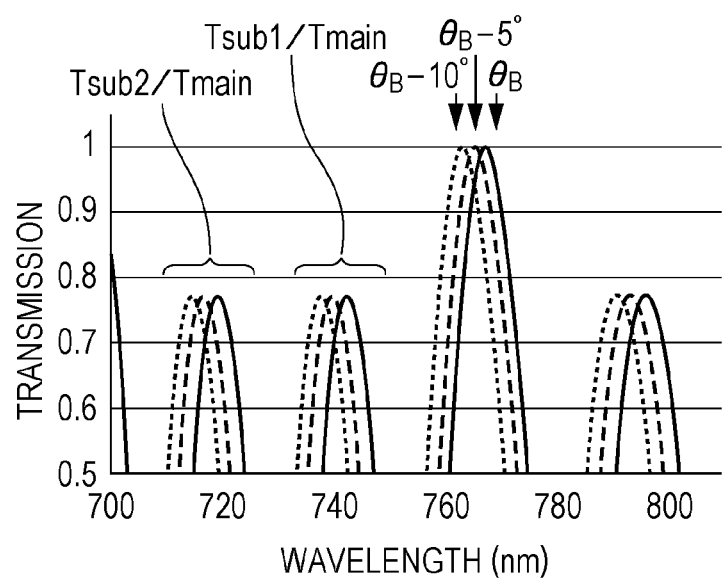
FIG. 7 illustrates a transmission spectrum in the case where the principal dielectric axes of two birefringent plates are made to coincide with each other and the insertion angle is changed.

As a comparative example, FIG. 7 illustrates a transmission spectrum in the case where the principal dielectric axes of the first birefringent plate and the second birefringent plate coincide with each other and the insertion angle $\theta$ is changed. For ease of comparison, the transmission spectrum is normalized with respect to the transmission Tmain of the transmission peak. As illustrated in FIG. 7, when the principal dielectric axes coincide with each other, Tmain/Tsub1 or Tmain/Tsub2 is not changed even when the insertion angle $\theta$ is changed.

On the other hand, when the principal dielectric axes of the first birefringent plate and the second birefringent plate are shifted from each other at a shift angle $\Delta\phi$ of $-4°$, the ratio of the transmission at the transmission peak to the transmission at the second subpeak Tmain/Tsub2 increases as the insertion angle $\theta$ decreases as illustrated in FIG. 6B.

To be more specific, the ratio Tmain/Tsub of the transmission peak to a certain subpeak can be further increased by installing the birefringence filter, in which the principal dielectric axes are shifted such that the transmission at the certain subpeak decreases, at a position on the optical axis at an insertion angle smaller than Brewster's angle. Consequently, according to the second embodiment, the wavelength variable range can be further expanded by shifting the principal dielectric axes such that the transmission at the subpeak that is located at the edge of the wavelength variable range and at which $(\sigma sub-\sigma main)/\sigma main$ is largest decreases and the insertion angle $\theta$ of the birefringence filter falls with a range of $42°\leq\theta<\theta B$.

Figure 8A:
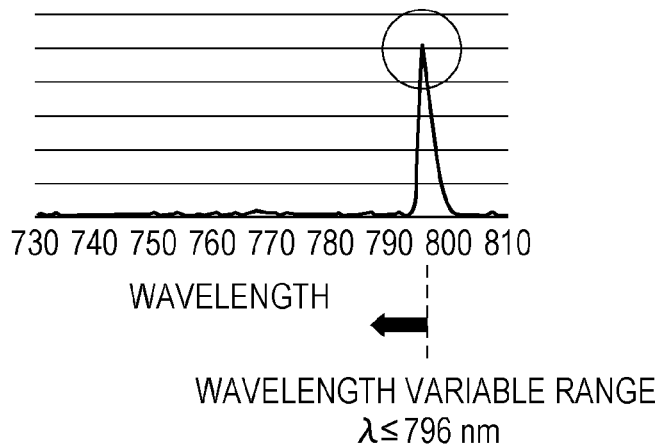
FIG. 8A illustrates an oscillation spectrum of a wavelength-variable alexandrite laser according to the second embodiment of the present invention.
Figure 8B:
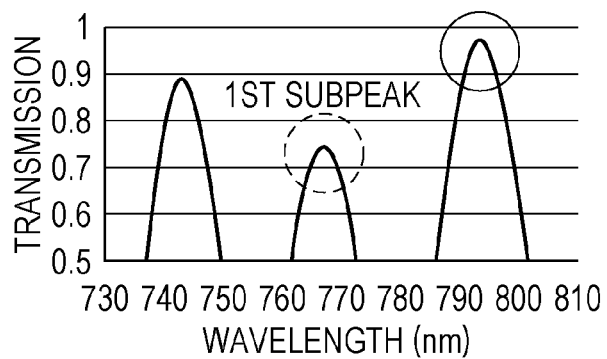
FIG. 8B illustrates a transmission spectrum of a birefringence filter.
Figure 8C:
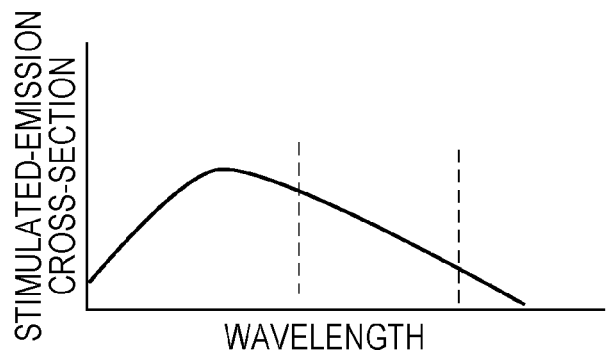
FIG. 8C illustrates a stimulated-emission cross-section of a gain medium.

Referring now to FIGS. 8A, 8B, and 8C, a tunable laser according to the second embodiment will be specifically described.

The tunable laser according to the embodiment is an alexandrite tunable laser and is required to have a wavelength variable range ranging approximately from 740 to 800 nm as in the case of the first embodiment.

In the wavelength variable range, the reflectivity of the highly reflecting mirror is 99% or more and the reflectivity of the partially reflecting mirror is approximately 70%. The highly reflecting mirror and the partially reflecting mirror face each other approximately 45 cm apart from each other with the gain medium interposed therebetween.

The birefringence filter includes a first birefringent plate and a second birefringent plate, which are crystal plates having principal dielectric axes parallel to the optical surfaces.

The thicknesses of the first birefringent plate and the second birefringent plate are 0.762 mm and 1.524 mm, respectively. Here, an interval between transmission peaks in or adjacent to the wavelength variable range is approximately 90 nm, which is larger than the width of the wavelength variable range (approximately 60 nm).

FIGS. 8B and 8C respectively illustrate the transmission spectrum of the birefringence filter and the stimulated-emission cross-section of alexandrite crystal. When the transmission peak is located at the wavelength of approximately 800 nm near the edge of the wavelength variable range, $(\sigma sub-\sigma main)/\sigma main$ is largest at the first subpeak. Thus, in the embodiment, the principal dielectric axes are shifted at the shift angle $\Delta\phi$ of 3° such that the transmission at the first subpeak decreases.

The birefringence filter is interposed between the gain medium and the partially reflecting mirror such that the insertion angle $\theta$ is smaller than Brewster's angle. In FIGS. 8B and 8C, Brewster's angle $\theta B$ of crystal in the wavelength variable range is 57° while the insertion angle $\theta$ of the birefringence filter is set at 50°.

FIG. 8A is the oscillation spectrum of the wavelength-variable alexandrite laser. As illustrated referring to FIG. 6A, when the insertion angle $\theta$ of the birefringence filter is set at 50°, the ratio of the transmission at the transmission peak to the transmission at the first subpeak Tmain/Tsub1 can be further increased than that in the case where the insertion angle is the same as the Brewster's angle $\theta B$. Consequently, the longer wavelength side edge of the wavelength variable range is capable of being expanded to the 796 nm.

Thus far, the case where the edge of the wavelength variable range is at the wavelength of 800 nm has been described, but the wavelength variable range may be a different wavelength range.

For example, the case is considered where a tunable laser in which alexandrite crystal is used as a gain medium and the wavelength variable range approximately ranges from 720 to 760 nm is designed. Here, (σsub−σmain)/σmain is largest at the second subpeak, at which the wavelength is approximately 720 nm, at the edge of the wavelength variable range. Thus, the smaller wavelength side edge of the wavelength variable range can be further expanded by, for example, shifting the principal dielectric axes of birefringent plates such that the shift angle Δϕ is −3° and making the insertion angle θ of the birefringence filter smaller than the Brewster's angle so that the transmission at the second subpeak is reduced.

The thickness of the second birefringent plate has been described in the above description of the embodiments as being two times the thickness of the first birefringent plate. However, the effect of the present invention can be obtained as long as the thickness of the second birefringent plate is an integral multiple of the thickness of the first birefringent plate.

Figure 9A:
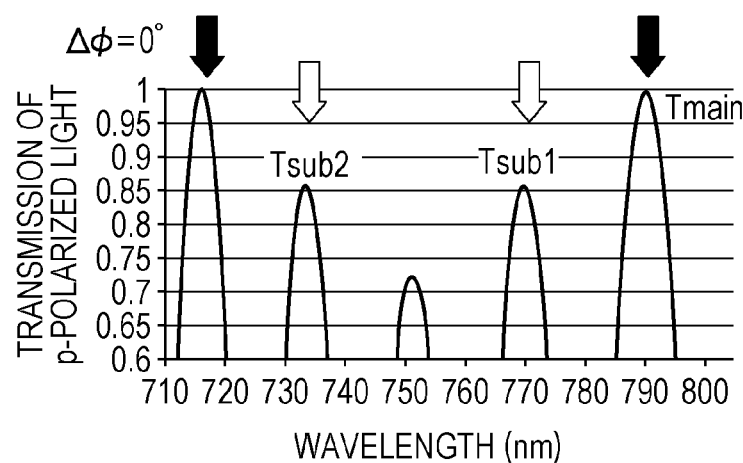
FIGS. 9A and 9B illustrate transmission spectra according to the second embodiment of the present invention.

FIG. 9A illustrates a transmission spectrum in the case, where the thickness of the second birefringent plate is set to be approximately three times the thickness of the first birefringent plate and the first and second plates are superposed at the shift angle Δϕ of 0°.

In the transmission spectrum of FIG. 9A, the transmission peaks (indicated by solid arrows) at which the transmission is 100% and subpeaks (indicated by hollow arrows) at which the transmission is second largest are shown.

Figure 9B:
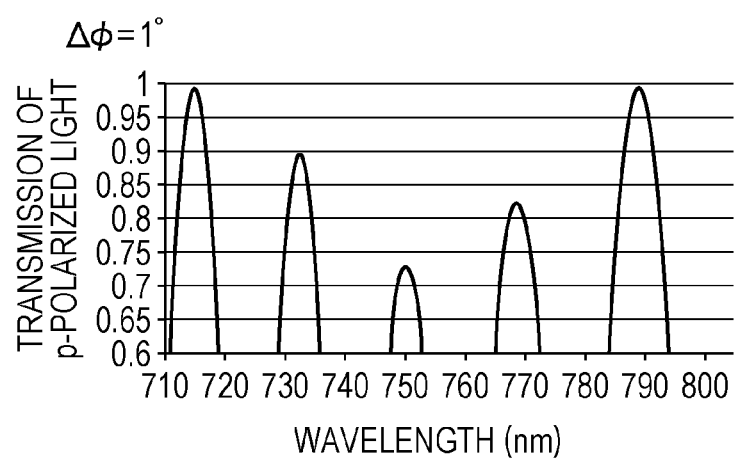

FIG. 9B illustrates a transmission spectrum in the case where the thickness of the second birefringent plate is three times the thickness of the first birefringent plate and the shift angle Δϕ is set at 1°.

Similarly to the first embodiment, in the second embodiment, the transmission at the first subpeak can be reduced by shifting the principal dielectric axis of the second birefringent plate and the principal dielectric axis of the first birefringent plate from each other at the shift angle Δϕ. Further, when the transmission ratio Tmain/Tsub is increased by making the insertion angle θ of the birefringence filter smaller than Brewster's angle, the wavelength variable range can be further expanded.

Generally, the transmission of subpeaks increases when the thickness of the second birefringent plate is two or more times the thickness of the first birefringent plate. Thus, it is preferable in terms of expansion of the wavelength variable range that the thickness of the second birefringent plate be two times the thickness of the first birefringent plate.

The thickness of the second birefringent plate has been described as being an integral multiple of the thickness of the first birefringent plate. However, the present invention can be embodied even when there is some tolerance in thickness of birefringent plates, as long as transmission peaks and subpeaks are efficiently found.

Figure 10A:
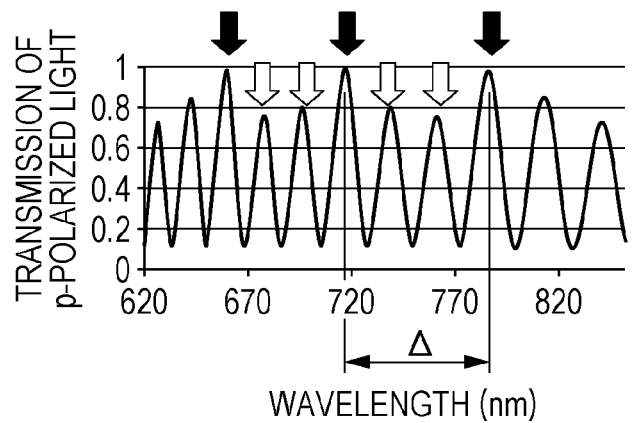
FIGS. 10A and 10B illustrate the tolerance in thickness of the birefringent plate according to the second embodiment of the present invention.

FIG. 10A illustrates a transmission spectrum of the birefringence in the case where the thickness of the second birefringent plate is 2.2 times the thickness of the first birefringent plate.

As in the case where the thickness of the second birefringent plate is two times the thickness of the first birefringent plate, transmission peaks (indicated by solid arrows) and subpeaks (indicated by hollow arrows) can be found in the transmission spectrum in FIG. 10A.

Figure 10B:
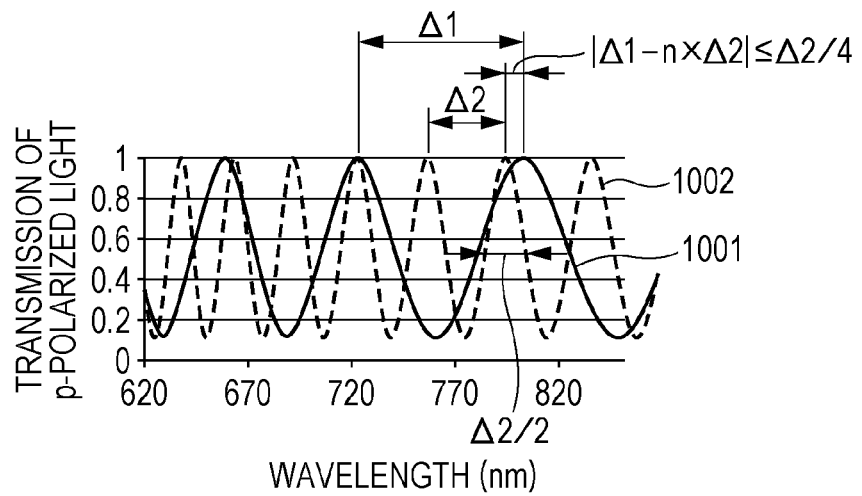
Figure 11:
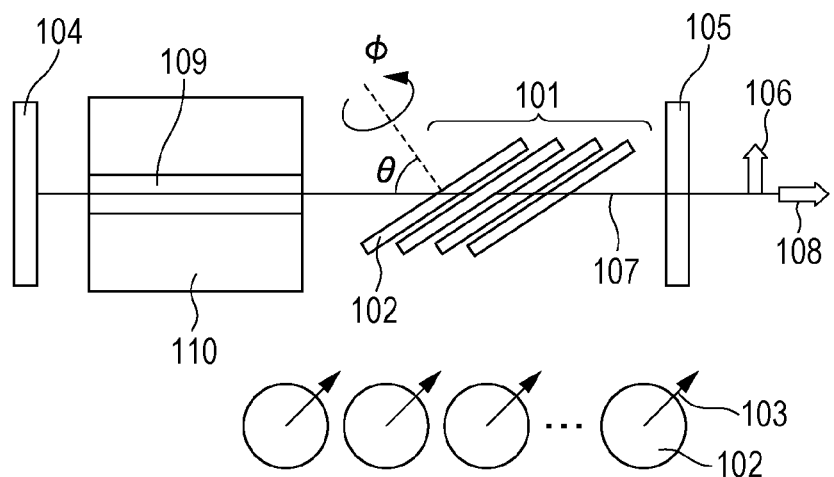
FIG. 11 schematically illustrates a configuration of a tunable laser including an existing birefringence filter.
Figure 12:
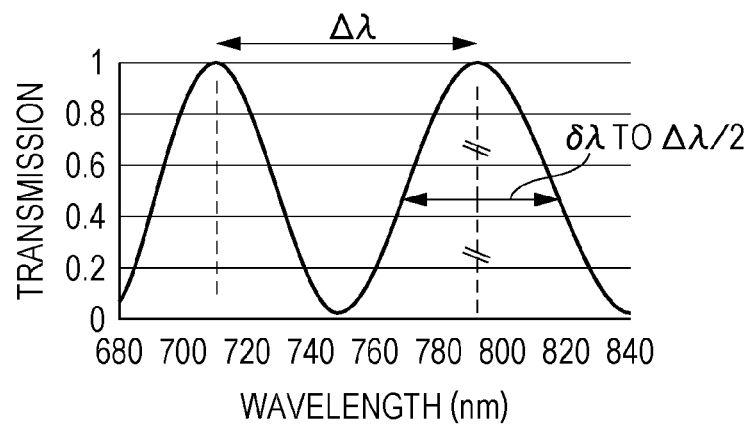
FIG. 12 illustrates a transmission spectrum of a birefringence filter including one birefringent plate.

FIG. 10B illustrates examples of a transmission spectrum 1001 of the first birefringent plate and a transmission spectrum 1002 of the second birefringent plate in the case where the thickness of the second birefringent plate is n+δn times (where n is an integer larger than or equal to two) the thickness d of the first birefringent plate.

Generally, the wavelength interval between the transmission peaks of the first birefringent plate is expressed as $\Delta T1 \propto 1/d$ and the wavelength interval between the transmission peaks of the second birefringent plate is expressed as $\Delta T2 \propto 1/d(n+\delta n)$.

As illustrated in FIG. 10B, a difference between transmission peaks in the transmission spectra of the first birefringent plate and the second birefringent plate is expressed as $|\Delta T1 - n \times \Delta T2|$.

When $\delta n = 0$, $|\Delta T1 - n \times \Delta T2| = 0$, and thus the transmission at the transmission peak of the birefringence filter is one. As is clear from FIG. 10B, when the peak difference $|\Delta T1 - n \times \Delta T2|$ is half the full width $\Delta T2/2$ at half maximum corresponding to the transmission peak of the second birefringent plate, that is, approximately $\Delta T2/4$ or smaller, the transmission peaks of the transmission spectra of the birefringent plates can be regarded as substantially coinciding with each other.

In other words, when the tolerance δn/n of the thickness of the second birefringent plate satisfies $\delta n/n \leq \frac{1}{4}n$, transmission peaks and subpeaks of the birefringence filter can be found in the transmission spectrum.

Thus, when the thickness of the first birefringent plate is denoted by d and n denotes an integer larger than or equal to two, if the thickness d2 of the second birefringent plate satisfies $(n-\frac{1}{4}n) \times d \leq d2 \leq (n+\frac{1}{4}n) \times d$, the thickness of the second birefringent plate is regarded as being approximately an integral multiple of the thickness of the first birefringent plate, whereby an effect according to the present invention can be obtained.

The tolerance is smaller than or equal to $\frac{1}{4}n = 0.125$ (12.5%) when n=2 or $\frac{1}{4}n = 0.083$ (8.3%) when n=3.

Although the case where one side edge of the wavelength variable range is expanded has been described in the embodiment, another side edge of the wavelength variable range can be similarly expanded as well. For example, a smaller wavelength side edge of the wavelength variable range can be expanded by shifting the principal dielectric axes such that the transmission at the subpeak at which (σsub−σmain)/σmain is larger decreases.

Moreover, both side edges of the wavelength variable range can be expanded.

For example, the following wavelength variable range is considered where (σsub−σmain)/σmain at the first subpeak is larger than that at the second subpeak on the first edge side, while (σsub−σmain)/σmain at the second subpeak is larger than that at the first subpeak on the second edge side.

Here, if the tunable laser is provided with an adjustment mechanism that adjusts the shift angle Δϕ of the birefringence filter, the shift angle Δϕ can be set to be positive on the first edge while negative on the second edge.

In addition, the case where alexandrite crystal is used as a gain medium has been described thus far, this is not the only possible configuration. Instead, titanium-sapphire crystal may be used as a gain medium.

Third Embodiment

Figure 15A:
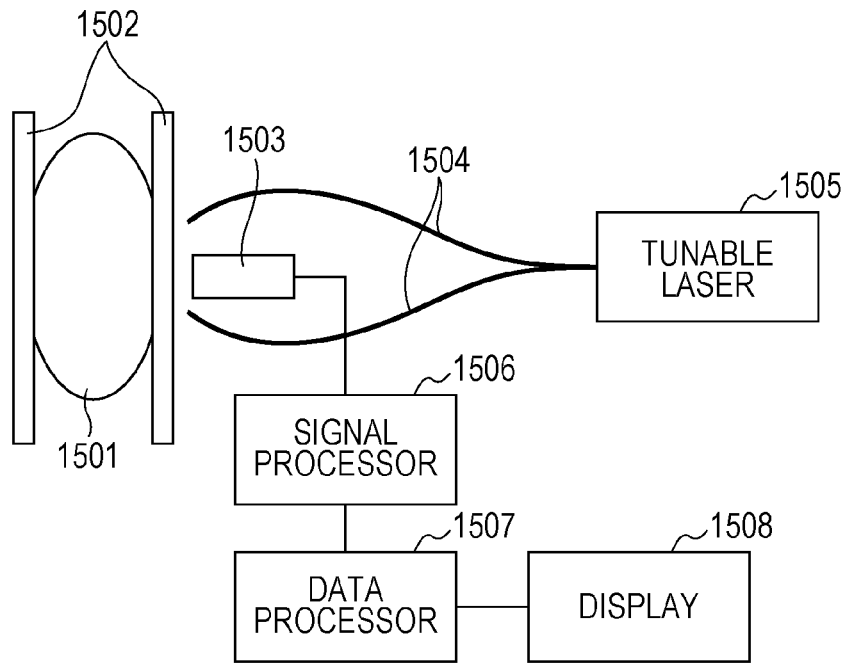
FIGS. 15A and 15B schematically illustrate a photoacoustic device according to an embodiment of the present invention.

FIG. 15 illustrates a photoacoustic mammographic device according to an embodiment in which the alexandrite laser according to an embodiment of the present invention is used as a light source of the photoacoustic device based on the principle of the photoacoustic tomography (PAT). FIG. 15A schematically illustrates a measurement portion of the photoacoustic mammographic device in the state where a breast 1501, which is an object, is fixed by being lightly compressed by fixing flat plates 1502. The measurement portion includes a probe 1503 and lighting portions 1504, provided on both sides of the probe 1503 so as to face each other. The measurement portion performs measurement by scanning the fixing flat plates 1502 using the probe 1503 and the lighting portions 1504 together. The lighting portions 1504 are connected to a tunable laser 1505 that switches the wavelength by operating the birefringent plates with any of the methods described above in the embodiments. The light output from the tunable laser 1505 is emitted to the breast 1501 via the lighting portions 1504. The tunable laser 1505 selectively outputs light of two different wavelengths λ1 and λ2. Oxyhemoglobin ($HbO_2$) and deoxyhemoglobin (Hb) inside the breast 1501 absorb the light output from the tunable laser 1505 and thus cause photoacoustic waves. Hereinbelow, such light emitted for causing photoacoustic waves is referred to as excitation light. The photoacoustic waves thus caused are detected by the probe 1503, converted into electric signals, and output to a signal processor 1506. The signal processor 1506 performs signal processing on the input electric signals, such as A/D conversion or amplification, and outputs the resultant signals to a data processor 1507. On the basis of the input signals, the data processor 1507 obtains object information (object information that reflects optical characteristics of the object such as an optical absorption coefficient) as image data. A display 1508 displays images on the basis of the image data input from the data processor 1507.

Figure 15B:
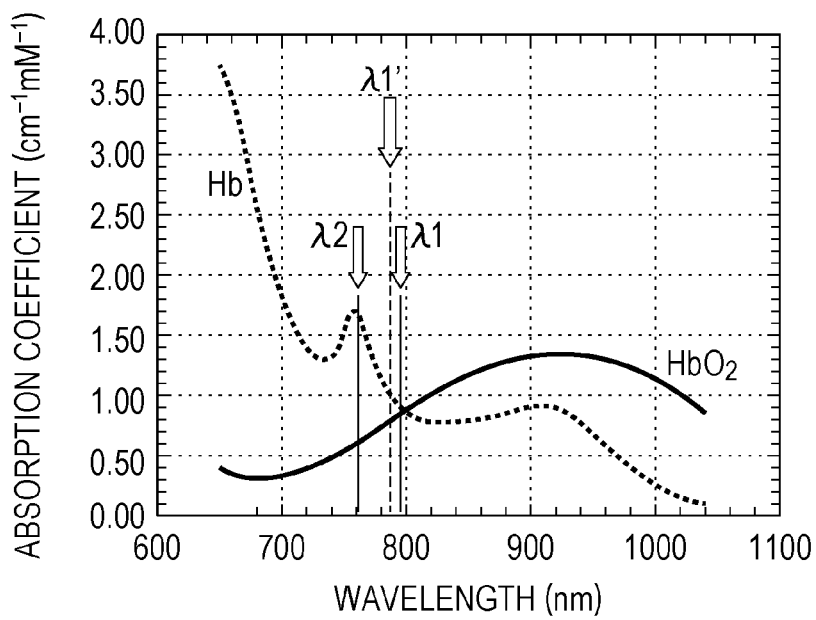

Such a photoacoustic mammographic apparatus can perform measurement over a wide range in a short time by scanning the object with the lighting portions 1504 while switching the wavelength such that the tunable laser 1505 outputs light of a wavelength λ1 while scanning in one direction and light of a wavelength λ2 while scanning in the other direction. In the case where alexandrite crystal is used as a gain medium of the tunable laser 1505 and the wavelength of output light is switched by operating two birefringent plates, the wavelengths λ1 and λ2 of the output light can be selected as 756 nm and 796 nm, respectively. FIG. 15B illustrates an absorption spectrum of oxyhemoglobin ($HbO_2$) and deoxyhemoglobin (Hb). Arrows λ1 and λ2 in FIG. 15B indicate two wavelengths (756 nm and 796 nm) in the case where the tunable laser according to an embodiment of the present invention is used. An arrow λ1' in FIG. 15B indicates a wavelength of output light of the tunable laser (λ1'=786 nm) in the case where the tunable laser according to an embodiment of the present invention is not used. The existing tunable laser including alexandrite crystal as a gain medium cannot select light having a wavelength longer than 786 nm when switching the wavelength by operating two birefringent plates. As is clear from FIG. 15B, an absorption coefficient difference $\alpha_{Hb}$ (786 nm)–$\alpha_{HbO2}$ (786 nm) is not zero in the case where the existing tunable laser is used. On the other hand, in the case where the tunable laser according to an embodiment of the present invention is used, an absorption coefficient difference $\alpha_{Hb}$ (796 nm)–$\alpha_{HbO2}$ (796 nm) is substantially zero. Thus, by using the output of the tunable laser according to an embodiment of the present invention as excitation light of a photoacoustic mammographic device, errors that can occur during imaging in vivo distribution of oxyhemoglobin ($HbO_2$) and deoxyhemoglobin (Hb) can be reduced.

According to an embodiment of the present invention, a tunable laser that includes a birefringence filter including two birefringent plates, that can reduce the transmission of subpeaks, and that can expand the wavelength variable range can be accomplished. In addition, a photoacoustic device including the tunable laser according to an embodiment of the present invention can produce a clear diagnostic image by using an output of the tunable laser according to an embodiment of the present invention as excitation light of the photoacoustic device.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-001118, filed Jan. 8, 2013, which is hereby incorporated by reference herein in its entirety.

What is claimed is:

1. A tunable laser comprising:
a first mirror and a second mirror;
a gain medium arranged between the first mirror and the second mirror;
a birefringence filter arranged between the first mirror and the second mirror; and
an excitation device exciting the gain medium,
wherein light that passes through the birefringence filter oscillates between the first mirror and the second mirror,
wherein an oscillation wavelength is switched by rotating the birefringence filter,
wherein the birefringence filter includes a first birefringent plate and a second birefringent plate, which have principal dielectric axes parallel to optical surfaces thereof, and
wherein, in a transmission spectrum of the birefringence filter in a case where an angle formed by a principal dielectric axis of the first birefringent plate and a principal dielectric axis of the second birefringent plate is zero, when peaks at which a transmission is highest are defined as main peaks, peaks at which a transmission is second highest are defined as subpeaks, a stimulated-emission cross-section of the gain medium at the main peaks is denoted by σmain, and a stimulated-emission cross-section of the gain medium at the subpeaks is denoted by σsub, the principal dielectric axes of the first birefringent plate and the second birefringent plate are shifted from each other so that, at the subpeak at which (σsub−σmain)/σmain is largest, a relationship ln(1/R)×(σsub−σmain)/2σmain<ln(Tmain/Tsub) is satisfied, where a transmission at the subpeak is denoted by Tsub, a transmission at the main peaks is denoted by Tmain, and a reflectivity of the second mirror is denoted by R.

2. The tunable laser according to claim 1, wherein the principal dielectric axes of the first birefringent plate and the second birefringent plate are shifted from each other so that a relationship 0°<Δϕ≤6° or −6°≤Δϕ<0° is satisfied, where a shift angle between the principal dielectric axes of the first birefringent plate and the second birefringent plate is denoted by Δϕ.

3. The tunable laser according to claim 2, wherein the gain medium is alexandrite crystal, and
wherein the principal dielectric axes of the first birefringent plate and the second birefringent plate are shifted from each other so that the shift angle Δϕ satisfies a relationship 5°≥|Δϕ|≥1°.

4. The tunable laser according to claim 1, wherein the birefringence filter is configured so that a relationship 42°≤θ≤θB is satisfied, where an insertion angle, which is an angle formed by a normal on an optical surface of the birefringence filter and an optical axis of the light, is denoted by θ and Brewster's angle of the birefringence filter is denoted by θB.

5. The tunable laser according to claim 1, wherein a thickness of the second birefringent plate is approximately two times a thickness of the first birefringent plate.

6. The tunable laser according to claim 1, wherein a thickness $d_2$ of the second birefringent plate satisfies a relationship $(n-\frac{1}{4}n) \times d \leq d_2 \leq (n+\frac{1}{4}n) \times d$, where a thickness of the first birefringent plate is denoted by d and n is an integer larger than or equal to two.

7. The tunable laser according to claim 1, wherein the gain medium is alexandrite crystal or titanium-sapphire crystal.

8. The tunable laser according to claim 1, further comprising an adjustment mechanism that adjusts a shift angle between the principal dielectric axes of the first birefringent plate and the second birefringent plate.

9. The tunable laser according to claim 1, wherein the principal dielectric axes of the first birefringent plate and the second birefringent plate are shifted from each other so that a wavelength variable range of the tunable laser is from 740 to 800 nm.

10. The tunable laser according to claim 9, wherein the gain medium is alexandrite crystal.

11. The tunable laser according to claim 10, wherein the birefringence filter is configured so that a relationship $45° \leq \theta < 50°$ is satisfied.

12. The tunable laser according to claim 1, wherein the principal dielectric axes of the first birefringent plate and the second birefringent plate are shifted from each other so that the tunable laser oscillates a laser having an oscillation wavelength of 786 nm or larger.

13. A photoacoustic device comprising:
a light source that irradiates an object with light and causes photoacoustic waves; and
a probe that detects the photoacoustic waves,
wherein the light source is the tunable laser according to claim 1.

14. The photoacoustic device according to claim 13, wherein the gain medium of the tunable laser is alexandrite crystal.

15. A tunable laser comprising:
a first mirror;
a second mirror;
a gain medium arranged between the first mirror and the second mirror;
a birefringence filter arranged between the first mirror and the second mirror; and
an excitation device exciting the gain medium,
wherein light that passes through the birefringence filter oscillates between the first mirror and the second mirror,
wherein an oscillation wavelength is switched by rotating the birefringence filter,
wherein the birefringence filter includes a first birefringent plate and a second birefringent plate, which have principal dielectric axes parallel to optical surfaces thereof,
wherein a thickness of the second birefringent plate is different from a thickness of the first birefringent plate, and
wherein the principal dielectric axes of the first birefringent plate and the second birefringent plate are shifted from each other so that a relationship $5° \geq |\Delta\phi| \geq 1°$ is satisfied, where a shift angle between the principal dielectric axes of the first birefringent plate and the second birefringent plate is denoted by $\Delta\phi$.

16. The tunable laser according to claim 15, wherein a thickness of the second birefringent plate is approximately two times a thickness of the first birefringent plate.

17. The tunable laser according to claim 15, wherein a thickness d2 of the second birefringent plate satisfies a relationship $(n-\frac{1}{4}n) \times d \leq d2 \leq (n+\frac{1}{4}n) \times d$, where a thickness of the first birefringent plate is denoted by d and n is an integer larger than or equal to two.

18. A photoacoustic device comprising:
a light source that irradiates an object with light and causes photoacoustic waves; and
a probe that detects the photoacoustic waves,
wherein the light source is the tunable laser according to claim 9.

19. A tunable laser comprising:
a first mirror;
a second mirror;
a gain medium arranged between the first mirror and the second mirror;
a birefringence filter arranged between the first mirror and the second mirror; and
an excitation device exciting the gain medium,
wherein light that passes through the birefringence filter oscillates between the first mirror and the second mirror,
wherein an oscillation wavelength is switched by rotating the birefringence filter,
wherein the birefringence filter includes a first birefringent plate and a second birefringent plate, which have principal dielectric axes parallel to optical surfaces thereof,
wherein the principal dielectric axes of the first birefringent plate and the second birefringent plate are shifted from each other, and
wherein the birefringence filter is configured so that a relationship $42° \leq \theta \leq \theta B$ is satisfied, where an insertion angle, which is an angle formed by a normal to an optical surface of the birefringence filter and an optical axis of the light, is denoted by $\theta$ and Brewster's angle of the birefringence filter is denoted by $\theta B$.

20. A photoacoustic device comprising:
a light source that irradiates an object with light and causes photoacoustic waves; and
a probe that detects the photoacoustic waves,
wherein the light source is the tunable laser according to claim 19.

* * * * *